United States Patent
McLaughlin

(10) Patent No.: US 6,220,244 B1
(45) Date of Patent: Apr. 24, 2001

(54) CONSERVING DEVICE FOR USE IN OXYGEN DELIVERY AND THERAPY

(76) Inventor: Patrick L. McLaughlin, 516 12th Ave., Salt Lake City, UT (US) 84103

(*) Notice: Subject to any disclaimer, the term of this patent is extended or adjusted under 35 U.S.C. 154(b) by 0 days.

(21) Appl. No.: 09/153,545

(22) Filed: Sep. 15, 1998

(51) Int. Cl.$^7$ .................................................. A61M 16/00
(52) U.S. Cl. .............................. 128/204.23; 128/204.21; 128/204.18; 128/205.24
(58) Field of Search ........................ 128/204.18, 204.21, 128/204.23, 204.26, 205.24, 207.16

(56) References Cited

U.S. PATENT DOCUMENTS

| | | | |
|---|---|---|---|
| 4,414,982 | 11/1983 | Durkan | 128/716 |
| 4,461,293 | 7/1984 | Chen | 128/204.23 |
| 4,462,398 | 7/1984 | Durkan et al. | 128/200.14 |
| 4,519,387 | 5/1985 | Durkan et al. | 128/204.23 |
| 4,611,591 * | 9/1986 | Inui et al. | 128/204.21 |
| 4,873,971 | 10/1989 | Perkins | 128/201.23 |
| 4,971,049 | 11/1990 | Rotariu et al. | 128/204.21 |
| 5,048,515 | 9/1991 | Sanso | 128/204.26 |
| 5,099,837 | 3/1992 | Russel, Sr. et al. | 128/204.26 |
| 5,129,390 | 7/1992 | Chopin et al. | 128/204.21 |
| 5,165,397 | 11/1992 | Arp | 128/204.21 |
| 5,280,780 | 1/1994 | Abel | 128/203.14 |
| 5,348,001 * | 9/1994 | Danon | 128/205.24 |
| 5,368,019 * | 11/1994 | Latorraca | 128/204.21 |
| 5,373,842 | 12/1994 | Olsson et al. | 128/204.21 |
| 5,558,086 | 9/1996 | Smith et al. | 128/204.26 |
| 5,603,315 | 2/1997 | Sasso, Jr. | 128/204.18 |
| 5,626,131 | 5/1997 | Chua et al. | 128/204.23 |
| 5,685,296 | 11/1997 | Zdrojkowski et al. | 128/205.24 |
| 5,697,364 | 12/1997 | Chua et al. | 128/204.21 |

* cited by examiner

*Primary Examiner*—Glenn K. Dawson
(74) *Attorney, Agent, or Firm*—Morriss, Bateman, O'Bryant & Compagni

(57) ABSTRACT

A method and apparatus for conserving oxygen provided for oxygen therapy. The oxygen conserving delivery system includes a sensor for detecting inspiration efforts, and a microcontroller which is triggered by the sensor to open a valve to allow the flow of oxygen to the patient. The system includes a cross-field excitation/detection inspiration sensor using an adaptive full-wave signal detector/tracer. The system also includes a method for conserving energy by a unique combination of start and sustain drive lines coupled to the valve control. The system is able to compensate for variations in battery condition, inlet gas pressures, variations in valve tolerances, and the absence of gas pressure in a fault condition. Finally, a self-adaptive inspiration depth tracking ability ensures constant oxygen delivery volume even when there are variations in inspiration depths rather than changes in respiration rates. This ability enables the system to provide oxygen at a depth and a rate which is a best fit for a patient's oxygen needs when at rest or at work.

20 Claims, 12 Drawing Sheets

CONSERVING DEVICE FOR USE IN OXYGEN DELIVERY AND THERAPY

BACKGROUND

1. The Field of the Invention

This invention relates generally to the administration of a supplemental, intermittent oxygen supply to a patient. More specifically, the present invention provides a method and apparatus for providing oxygen therapy to a patient, where a system includes the ability to conserve oxygen by only delivering an amount that is usable by the patient during an inspiration cycle.

2. The State of the Art

The state of the art in oxygen therapy is replete with systems that attempt to conserve oxygen being supplied to a patient. The need to conserve oxygen is a result of the understanding that continuous, long term oxygen therapy is expensive because of the large quantities of oxygen that needed to be provided to a patient.

Less sophisticated oxygen therapy systems provide oxygen at a continuous rate without interruption. The result is that all oxygen supplied to the patient during exhalation is wasted. This waste can be substantial considering that approximately two thirds of the respiratory cycle is spent in exhalation. Furthermore, these systems do not adjust for rates or depth of inspiration by the patient. These factors, combined with the fact that the oxygen therapy is generally being conducted using a mobile oxygen container, demonstrate the need for more prudent oxygen conservation. Clearly what is needed is a way to reduce oxygen consumption while maintaining adequate alveolar gas exchange of the patient.

To meet this need for oxygen conservation during oxygen therapy, systems have been developed which are designed to deliver oxygen only during patient inspiration. However, the methods and apparatus for accomplishing this goal are many, and are met with varying degrees of success.

One method for accomplishing conservation during oxygen therapy is to provide pulsed oxygen delivery to the patient according to some control logic based upon a physician prescribed gas flow rate and the breathing characteristics of the patient. For example, studies support the observation that the first portion of inspiration is the most effective time for oxygen delivery, with the last portion of the patient's inspiration not actually providing oxygen to the secondary respiratory system (i.e. the blood stream).

For example, in U.S. Pat. No. 5,165,397 issued to Arp, the patent apparently teaches a method and apparatus for providing oxygen on demand, where the system is responsive to a patient's breathing.

Similar systems are taught in U.S. Pat. No. 5,099,837 issued to Russel Sr. et al., and in U.S. Pat. No. 5,697,364 issued to Chua et al. All of these systems have numerous drawbacks which prevent them from serving all the functions of an acceptable oxygen conservation device. These drawbacks include, but are not limited to, a failure to adequately adapt to breathing depth (force) of the person using the system. They also fail to take into account changes that occur due to variations in altitude of the user. They also fail to compensate for changes in battery strength, and fail to adequately conserve battery power.

It would be advantageous over the state of the art in oxygen therapy to provide a conserving device which is responsive to the breathing rate of the patient. The system should adapt the volume of oxygen delivered depending upon depth of inspiration, and the rate of inspiration.

It would also be advantageous to provide a conserving device which did not require training of the patient, so that the system was responsive to the patient, and not the other way around.

The system should be capable of making some adjustments to patient inspiration, regardless of whether the patient's inspiration rate or depth changes rapidly.

It would also be an improvement over the state of the art to provide a system which does not require a plurality of oxygen delivery tubes between the conserving device and the patient.

OBJECTS AND SUMMARY OF THE INVENTION

It is an object of the present invention to provide a method and apparatus for providing oxygen therapy which results in a reduction or elimination of variations in oxygen flow.

It is another object to provide a method and apparatus for providing a dynamically adaptive delivery of oxygen flow to the patient to thereby better respond to a patient's changing needs.

It is another object to provide a mobile conserving device for use in oxygen therapy which reduces power consumption to thereby extend the life of a battery providing power.

The presently preferred embodiment of the present invention is a method and apparatus for conserving oxygen provided for oxygen therapy. The oxygen conserving delivery system includes a sensor for detecting inspiration efforts, and a microcontroller which is triggered by the sensor to open a valve to allow the flow of oxygen to the patient. The system includes a cross-field excitation/detection inspiration sensor using an adaptive full-wave signal detector. The system also includes a method for conserving energy by a unique combination of start and servo sustain drive lines coupled to the valve control. This method of conserving energy also includes the ability to compensate for variations in battery condition, inlet gas pressures, variations in valve tolerances, and the absence of gas pressure in a fault condition. Finally, a self-adaptive inspiration depth tracking ability ensures constant oxygen delivery volume even when there are variations in inspiration depths in addition to changes in respiration rates.

In a first aspect of the invention, a unique start and sustain servo is used for the valve which enables the microcontroller to use a minimum amount of energy from the power source to open the valve for each pulse of oxygen that flows therethrough.

In another aspect of the invention, this start and sustain method of valve operation automatically controls energy consumption by compensating for a diminishing power factor curve that is associated with batteries. This method also allows for automatic compensation of performance variations within the valves themselves.

In another aspect of the invention, electro motive energy which is reflected form the valve is shunted back to the battery to further conserve energy.

In another aspect of the invention, the sensor responds to the entire phase of the patient's respiration efforts and the admission cycle of the oxygen. This is accomplished by calculating a real-time respiration depth-time factor. A system for calculating the depth-time factor is stored as a schedule for providing a constant percentage ratio between inspiration depth time and actual valve on-times, or a sliding bolus. Using this depth-time factor coupled with monitoring the respiration rate, the system is able to provide proper oxygen delivery while compensating for changing respiration activities which change both rate and depth of patient inspiration.

These and other objects, features, advantages and alternative aspects of the present invention will become apparent to those skilled in the art from a consideration of the following detailed description taken in combination with the accompanying drawings.

DETAILED DESCRIPTION OF THE INVENTION

Reference will now be made to the drawings in which the various elements of the present invention will be given numerical designations and in which the invention will be discussed so as to enable one skilled in the art to make and use the invention. It is to be understood that the following description is only exemplary of the principles of the present invention, and should not be viewed as narrowing the claims which follow.

Before describing the invention, it is useful to remember from the outset that this technology has application in both the medical and aviation fields. This is because the same adaptive method taught by the present invention for changing the oxygen delivery rate for a patient who is changing between an ambulatory state and an at-rest state can also be used to adapt an oxygen flow rate to a pilot or passenger based on changes in altitude.

Figure 1:
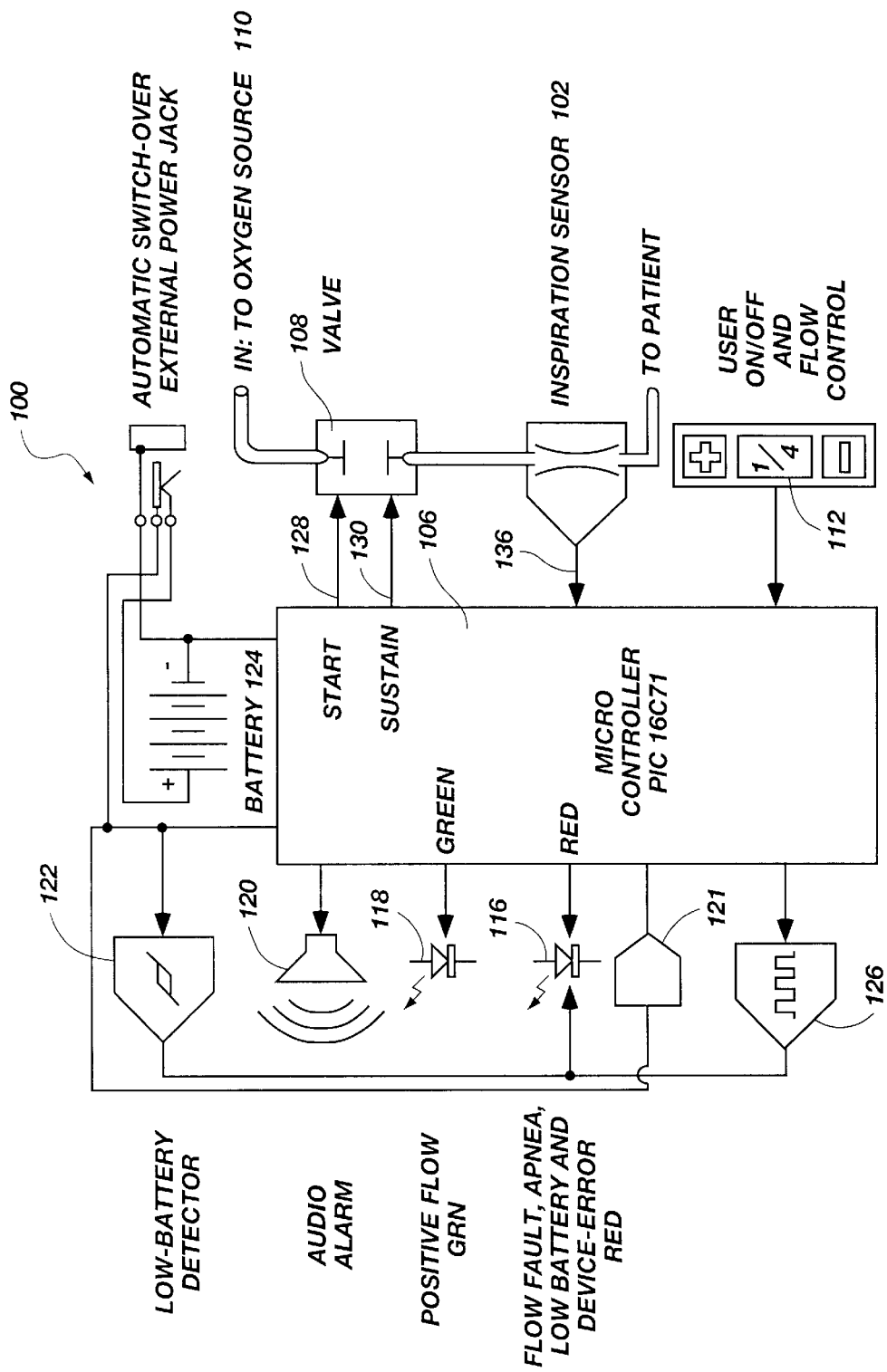
FIG. 1 is a block diagram of the presently preferred embodiment which is made in accordance with the principles of the present invention. The components of the conserving device are shown with respect to a patient and an oxygen source.

The preferred embodiment of the present invention is shown in the block diagram of FIG. 1. The oxygen conservation device 100 is shown to be comprised of several components. These components will be described by examining how the components interact during operation of the device.

An inspiration sensor assembly 102 includes an inspiration sensor 164 (not shown until FIGS. 4A and 4B) which detects inspiration efforts of the patient when the patient inhales. It is assumed that the patient has inserted in the nasal passages a cannula (not shown). The cannula is coupled to the inspiration sensor 164 via a single tube 104. The inspiration sensor 164 generates a signal to a microprocessor 106 (or any other appropriate microcontroller) when the patient begins a respiration cycle that is detected by the inspiration sensor 164. In response, the microprocessor 106 generates a signal which opens a valve 162 (FIG. 2) in a valve assembly 108. The opened valve 162 enables oxygen to flow for a short period of time from an oxygen source 110, through the valve 162, and on to the cannula through the tube 106. At the end of some predetermined or calculated duration, the valve 162 is closed. This cycle then repeats itself at the beginning of every inspiration effort of the patient. It is noted that the inspiration rate may be limited to, for example, 20, 25, 30 and 40 bpm. This is also known as hold-off.

In conjunction with the overview of the oxygen delivery process described above, the oxygen conservation device 100 has other useful features which enhance usability of the device. For example, a manually operable on/off switch 112 enables the user to turn off the flow of oxygen to the patient. This same switch 112 is also capable of operating as an effective rate of flow control switch. The amount of oxygen which is delivered to the patient can be set by the user so that an overall physician prescribed flow rate can be maintained under normal breathing conditions. The flow rate switch 112 turns off the device by setting the respiration rate to zero or to an "OFF" switch setting.

Status indicators also provide feedback to the user to indicate a condition of the oxygen conserving device 100 that requires attention. The status indicators include both visual indicator means 116, 118 and audio indicator means 120. As will be explained, these conditions include flow fault, apnea, low battery, device error, and positive flow. While the microprocessor 106 determines a condition of flow fault, apnea, and positive flow, a separate low voltage battery detector circuit 122 and a run-time device-error detector circuit 126 (watch dog circuit) are typically used for detection of these conditions. The system also includes a voltage integrity monitor 121, which should not be confused with the low voltage battery detector circuit 122.

In the presently preferred embodiment, the oxygen conserving device 100 is a mobile device which operates using a battery 124 as the power source.

It should be realized that the audio alarm means 120 can alert the user of a serious condition of the device 100 which requires immediate attention. However, for the visually impaired, the audio indicator means 120 can also function to provide the same feedback to the user as is provided by the visual indicator means 116, 118.

In the presently preferred embodiment, the visual indicator means 116 is a warning indicator and is thus selected to be a red light. In contrast, the visual indicator means 118 is used to provide feedback to the user about the flow of oxygen from the oxygen source 110, and is therefore selected to be a green light to indicate that there is a condition of positive flow.

It is noted that instead of the red and green indicator lights, the visual indicator means could also be displayed on a liquid crystal display (LCD). This alternative embodiment has the advantage of very low power consumption, and yet providing a very informative and detailed visual display.

In the presently preferred embodiment, the visual indicator means 116 and 118 are selected to be lights of any appropriate variety which can be driven by signals from the microprocessor 106. A diode symbol is used in FIG. 1, but this can be substituted. Those skilled in the art understand the appropriate voltages that can be supplied and used to drive the type of selected visual indicator.

The microprocessor selected for use in the presently preferred embodiment has a part number of PIC 16C71. However, it should be understood that any microcontrolling device that can be programmed in firmware can be substituted for this particular integrated circuit.

It should also be understood that the instructions for the microprocessor utilized in this presently preferred embodiment are stored in a memory device which is programmable. For example, an EEPROM (electrically erasable and programmable read-only memory) is associated with the microprocessor so that when the oxygen conserving delivery system is activated, the microprocessor prepares itself for use. Preparation includes an internal self-test of the OCDS, and then a one-time flow-fault check.

While some of the processes and indicator means described above are well known in the art, there are several aspects of these processes which are unique to the present invention. These novel aspects of the invention will become apparent while describing the components and operational detail of the oxygen conserving device 100.

Beginning with the operation of the valve 162, it is operated via two drive lines from the microprocessor 106. FIG. 1 shows that these drive lines are labeled a start drive line 128 and a sustain drive line 130.

Figure 2:
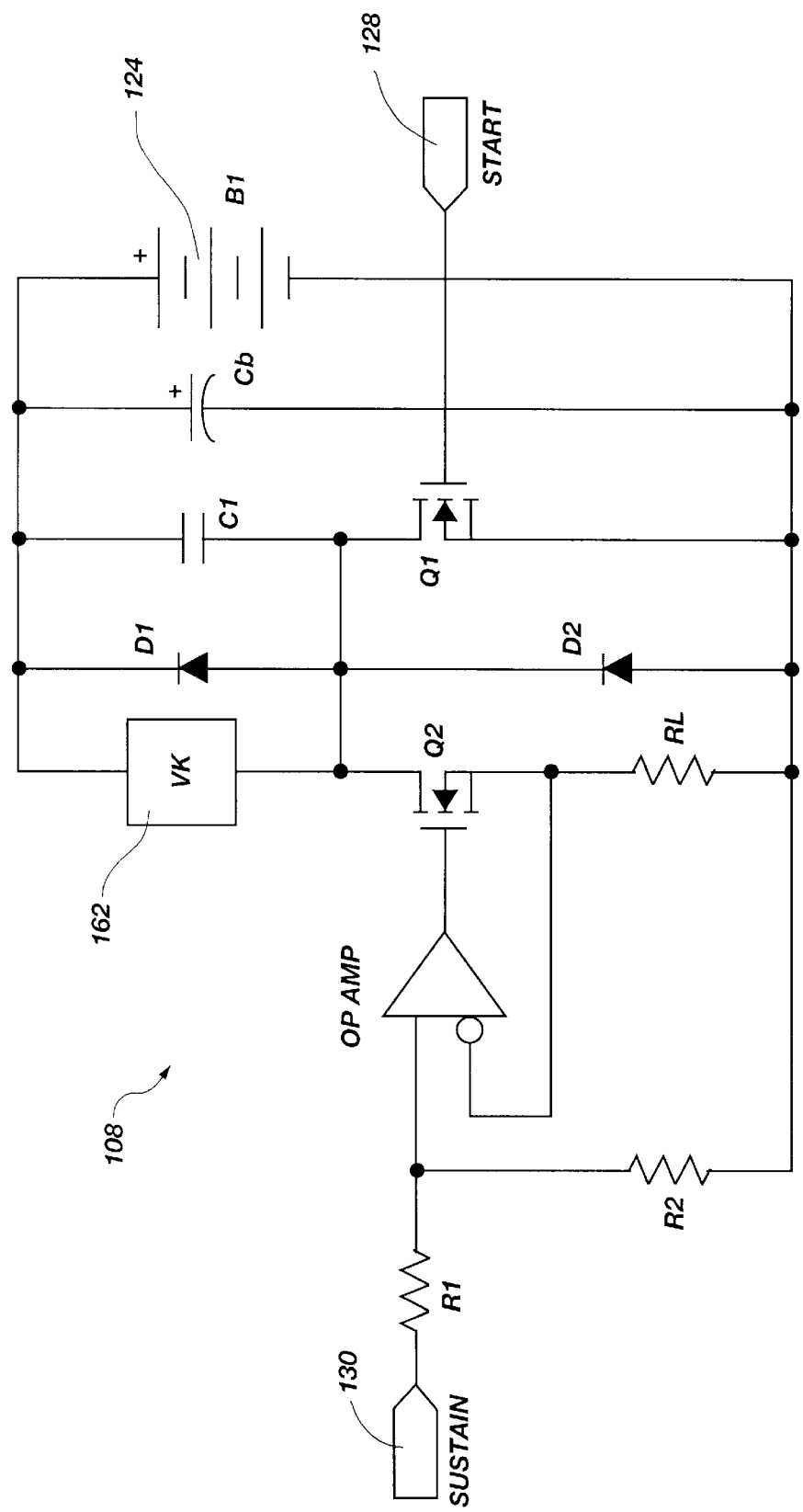
FIG. 2 is a schematic diagram illustrating a portion of circuitry included within the valve assembly shown in FIG. 1. This circuitry shows the interaction between the valve, the start and the sustain drive lines.

FIG. 2 is a schematic diagram illustrating the start drive line 128 from the microprocessor 106, the sustain drive line 130, and the valve assembly 108. The start drive line 128 is a high-current start pulse to meet the initial so-called "kick-in" higher power requirement that is generally associated with electromechanical devices. In contrast, the sustain drive line 130 is a lower (constant current) drive line that keeps the valve 162 energized in a lower power sustain mode once it has been opened by the higher current start drive line 128. The sustain drive line 130 advantageously provides a constant current to the valve 162 regardless of the condition of the battery's useful power factor.

The start and sustain drive line method operates as follows. The microprocessor 106 detects a signal from the inspiration sensor 164 indicating inhalation by the patient. The microprocessor 106 responds by activating the start drive line 128. The start drive line 128 initially energizes the valve 162 with the full voltage available from the battery supply 124. The valve 162 does not place an instantaneous full power load on the battery 124, but the power builds gradually until a reactance of the coil "exhibits" the electro motive energy required to open the valve 162.

Once the valve 162 has opened, the inspiration sensor 164 (FIG. 1) detects oxygen pressure. The start drive line 128 is then no longer needed, and it is de-energized by the microprocessor 106 so that the sustain drive line can take over during the duration of the on-time required by the valve 162. A typical ratio of "ON" time for the start drive line versus the sustain drive line is 8:1, where the sustain drive line is on the longest.

Reflected electromotive energy from the valve 162 is reverse shunted by the clamping diodes D1 and D2 which direct energy back into the circuit which includes the battery 124 and the damping capacitor C(b). The diodes D1 and D2 thus also serve as quenching arrestors of any potential electrical spark that may be generated by any back EMF events from the valve 162 while the transistors Q1 and Q2 release power being supplied to the valve. This ensures maximum safety of the oxygen conserving device 100 because of its potential use in oxygen rich environments.

This dual-line start and sustain drive line method of operating the valve 162 enables the microprocessor 106 to use only the amount of battery energy needed to open the valve and then maintain it in an open position. This is possible because the start drive line 128 is turned off by the microprocessor 106 once the valve 162 has been detected to be open. This method also enables the oxygen conserving device 100 to automatically compensate for a diminishing power factor curve that is associated with batteries, and to also compensate for variations of performance of the valve 162 itself.

The valve 162 of the presently preferred embodiment is a low-power electromechanical poppet type of valve. The valve 162 is normally closed when in a non-energized state. In the event of failure of the valve 162 or the oxygen conserving device 102, the valve will restrict any flow of oxygen to the patient. In this situation, the user must bypass the oxygen conserving device 100 by disconnecting the cannula and the oxygen source from the oxygen conserving device 100 and coupled the them together directly using a coupler barb, allowing oxygen to flow in a preset constant-flow configuration. In an open state, the valve 162 has a minimal amount of restriction on the net flow of oxygen, i.e. about 3%.

Figure 3:
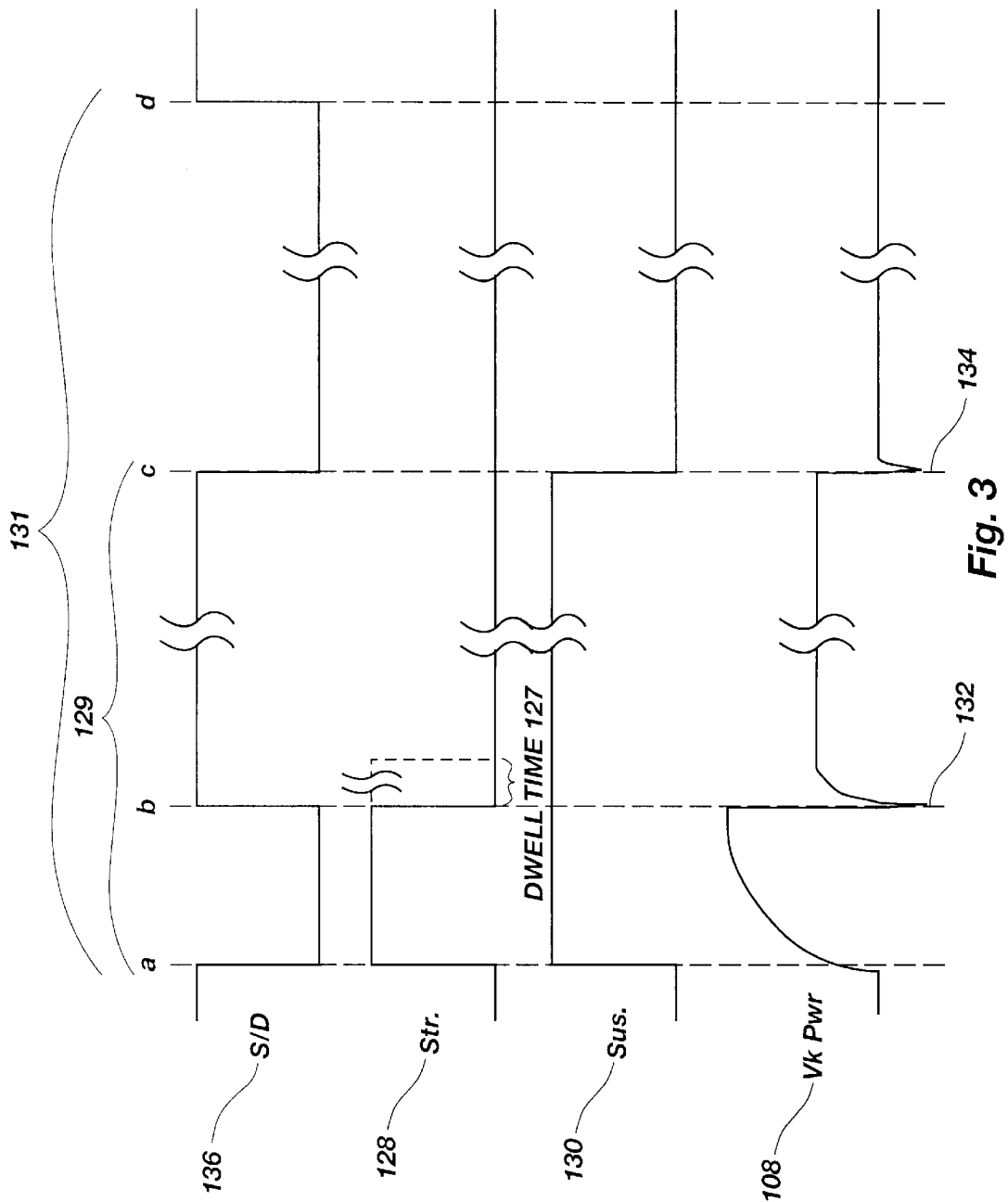
FIG. 3 is a simplified timing diagram which illustrates the cycles of operation of the oxygen conserving device of FIG. 1 including the inspiration sensor input, the start drive line, the sustain drive line, and the power being delivered to the valve.

FIG. 3 is provided as a simplified illustration of an event timing diagram which demonstrates the cycles of operation. It is important to keep in mind during this explanation that the inspiration sensor 164 continues to respond to all of the phases of a respiration cycle, as well as the pressure of oxygen.

At time mark (a), the inspiration sensor 164 detects the inspiration effort of the patient by going from high to low. The microprocessor drives both the start drive line 128 and the sustain drive line 130 high. Between time marks (a) and (b), the power consumed by the valve 162 is shown as increasing until reaching a peak at time mark (b) when the valve opens. A sensor output line (S/D) 136 returns to a high output when the oxygen pressure is detected from the oxygen source 110 (FIG. 1), and the start drive line 128 goes low as it is no longer needed. It should be realized that this return will dwell longer in proportion to reduced battery voltage. This dwell time 127 is shown as an unknown but typically short duration (on the order to approximately 5 to 10 ms) of time after the start drive line 128 is de-energized.

The time between time marks (b) and (c) is indicative of the on-time of the valve 162, while the time between time marks (c) and (d) is indicative of the remaining portion of the respiration cycle during which no oxygen is being supplied to the patient because the valve has closed at time mark (c).

The microprocessor 106 measures the time duration from time mark (a) through time mark (d) to thereby achieve a real-time respiration depth time factor. This time factor is used to help compensate for deep respiration efforts.

FIG. 3 indicates that the total "on" time of the valve 162 is shown as time 129 from time mark (a) to time mark (c). The time between inspiration events is shown as the time 131 from time mark (a) to time mark (d). What is not shown because of the lack of scale is that the time 131 is typically ten to twenty times longer than the time 129 during which time the valve is being actuated.

It is noted that the reflected electromotive energy is shunted back to the power supplying circuitry at time points 132 and 134 of FIG. 3.

Figure 4A:
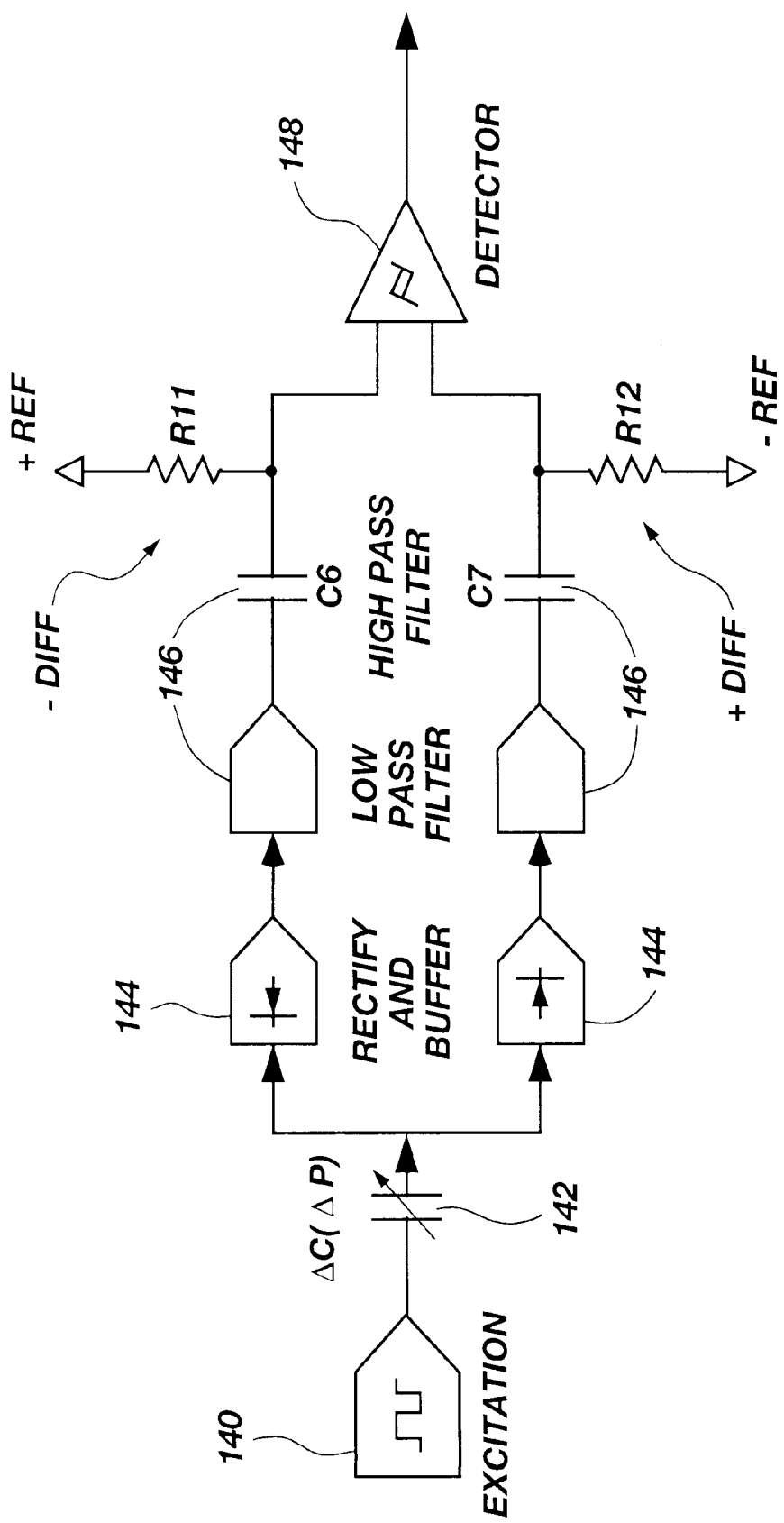
FIG. 4A is a block diagram of the inspiration sensor and its associated sensor circuitry which comprise the inspiration sensor assembly shown in FIG. 1.

FIG. 4A is a block diagram of the inspiration sensor 164 and its associated sensor circuitry. This diagram is helpful in understanding the overall purpose of the inspiration sensor without having to see the detail provided in FIG. 4B.

Without going into the detailed explanation, the inspiration sensor is comprised of the following components. First, an excitation circuit 140 provides a signal to the sensor 142. The sensor generates output signals which are indicative of pressure on the sensor. An output signal from the sensor 142 is then rectified and amplified (buffered) at 144. The signals are then sent through a low pass filter and a high pass filter at 146. The positive and negative difference signals are then sent to a detector 148.

Figure 4B:
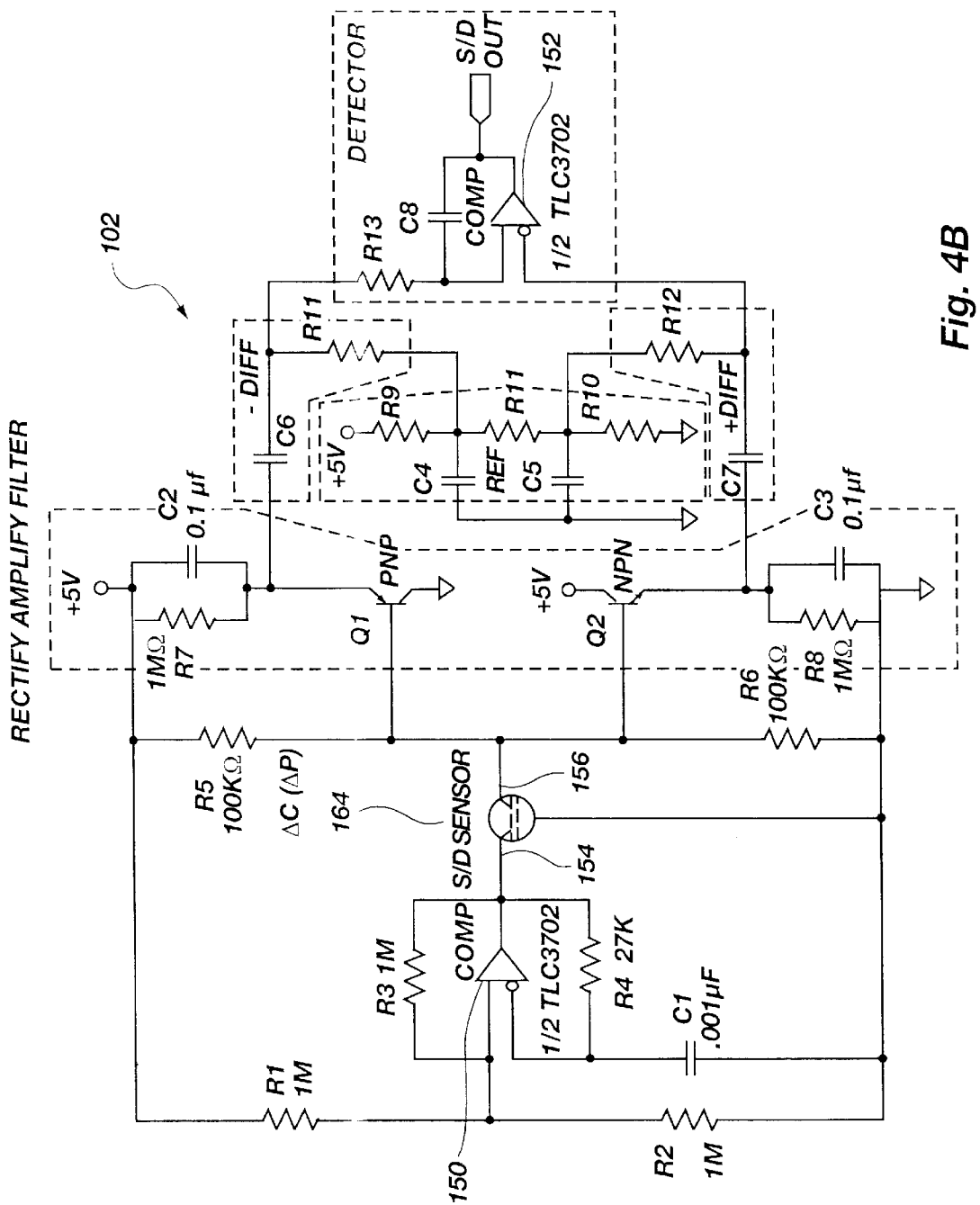
FIG. 4B is a schematic diagram of the inspiration sensor and its associated sensor circuitry which comprise the inspiration sensor assembly shown in FIG. 4A.

FIG. 4B is a more detailed schematic diagram of the inspiration sensor 164 and its associated sensor circuitry of the presently preferred embodiment. Some observations about this circuit are that a first comparator circuit 150 (which includes an operational amplifier) is used to generate a square-wave signal of 15 Khz. This signal is generated using passive components R1, R2, R3, R4 and C1. The suggested values (but not the only values possible) for these components are as follows: R1=1 mega ohm, R2=1 mega ohm, R3=1 mega ohm, R4=27 kilo ohm, and C1=0.001 micro farads. It is noted that a suitable part number for the operational amplifier used in the first comparator circuit is TLC3702.

The square wave signal from the first comparator circuit 150 is used to excite the inspiration sensor 164. In this preferred embodiment, the inspiration sensor 164 is a dual-plate stationary capacitor where a canter plate (moving membrane) is used to capacitively couple the two stationary plates. Changes in pressure move the membrane closer for negative pressures, and further apart for positive pressures because the capacitor plates are caused to couple or uncouple, respectively. The change in pressure results in more or less capacitively coupled current to flow from a driven stationary plate 154 to a receiving stationary plate 156 within the inspiration sensor 164.

The receiving stationary plate 156 is coupled to a full-wave rectifier/detector and current amplifier circuit that is comprised of passive components R5, R6, R7, R8, C2 and C3, and of active components Q1 and Q2. The suggested values for these components in this preferred embodiment are as follows: R5=100 kilo ohm, R6=100 kilo ohm, R7=1 mega ohm, R8=1 mega ohm, C2=0.1 micro farads, and C3=0.1 micro farads. Suitable transistors Q1 and Q2 can be selected with part numbers 2N3904, 2N3906 or their equivalent. Transistors Q1 and Q2 may be bipolar NPN type transistors.

The operational amplifier used in the second comparator circuit 152, which can be identical to the first comparator circuit 150, is used as a voltage comparator for detecting a voltage that is equal to or greater than a reference voltage. Dual reference voltages are generated by the resistor network R9, R10 and R11 for the second comparator resistors R11 and R12. Resistors R11 and R12 enable a drive impedance from the voltage divider network R9, R10 and R11 of about 2 mega ohms.

The output of the second comparator circuit 152 is held high while it is quiescent. Capacitors C6 and C7 are used as coupling capacitors that enable a differentiating counter-augment current to the high impedance dual reference voltage. In other words, complimentary signals having a given rate of change produced through the inspiration sensor 164 are then rectified and buffered to thereby augment the reference voltage so as to be detectable by the second comparator (detector) circuit 152. The resistor R13 in association with capacitor C8 give the second comparator 152 positive feedback so that a controlled amount of dynamic (mono stable) hysteresis ensures that the second comparator 152 generates a clean and jitter-free transition from a high-to-low and from low-to-high state for each valid threshold detection event. The voltage reference follows the amplitude of the square wave generator on a 1:1 basis so that variations in a supply voltage does not effect the relative and dynamic sensitivity of the entire excitation, sensor and rectifier/buffer system from 1.5 to 15 volts.

The rectifier/buffer circuitry generates complementary DC voltage outputs in an analog form which is representative of the absolute position of the membrane with respect to the stationary plates 154 and 156 and the amplitude of the square wave signal being generated by the first comparator circuit 150.

Regarding the operational parameters of the present invention, in this description of the preferred embodiment, it is noted that the oxygen conserving device 100 is powered via a 9 or a 3 volt battery. Alternatively, the oxygen conserving device can be operated from an AC power source using a transformer to generate DC voltage. In the event of AC power failure, unplugging the AC adapter will enable the battery to provide energy to the device.

The maximum operating inlet pressure for the oxygen conserving device 100 is approximately 50 psig. The maximum, non-operating, inlet pressure the device can tolerate without damage is approximately 115 psig. The oxygen conserving device 100 can also respond to inspiration efforts as measured at the sensor as low as 1 mm of $H_2O$.

The oxygen conserving device 100 has included therein a table for each flow setting that is selected. The table is based upon a formula for valve-on pulse outputs as follows:

$$VKt = \frac{\frac{flr(te)}{Ir}}{\frac{Vkf}{60}}$$

Where:
  Vkt=valve open dwell time in ms
  Vkf=valve open flow coefficient in liters/min
  flr=the desired prescribed flow rate in liters/min
  Ir=the effective inspiration rule (typically 500 ms) during which a person will benefit from all the oxygen that is available
  te=the standard temperature factor of 1.0 for 25 degrees C.

Figure 5:
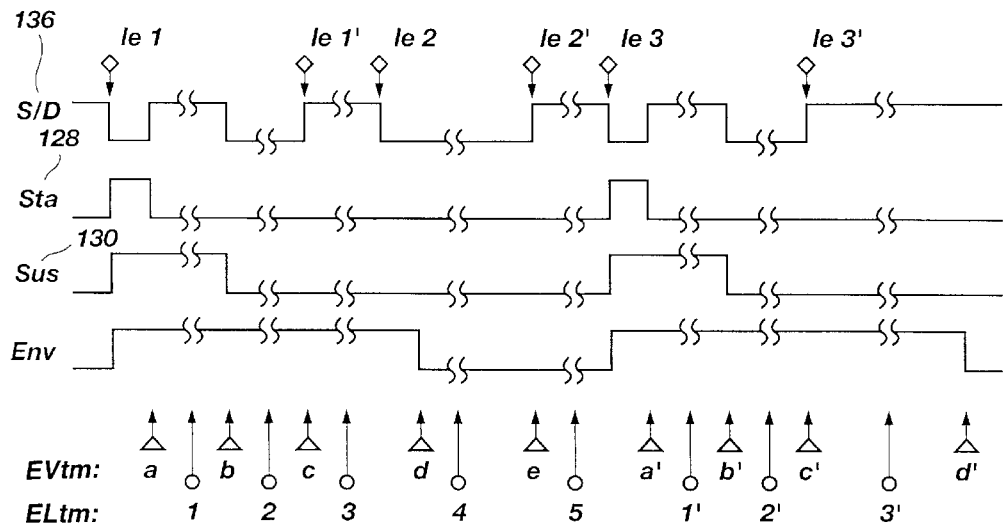
FIG. 5 is an event timing diagram showing operation of the oxygen conserving device of FIG. 1 under normal operating conditions.

FIG. 5 is provided because it is useful to examine normal operation of the oxygen conserving device 100 in terms of what should be considered an event timing diagram describing normal operation. The event timing diagram shows the start drive line (Sta) 128 and the sustain drive line (Sus) 130 that drive the valve 102, and an internal envelope signal (Env), all of which are generated in response to inspiration events (Ie) that are derived from the inspiration sensor output (S/D) 136. The Inspiration events are shown as diamonds, secondary time mark events are shown as triangles, and arbitrary elapsed times are indicated by circles. Event time mark (Evtm) points are alphabetically labeled, and Elapsed time mark points are numerically labeled.

The first inspiration event Ie(l) is indicated by the S/D sensor input line going low which starts the valve 162 energizing. After the valve 162 is energized, and opens to allow oxygen to flow, the S/D input line goes back high as a result of oxygen pressure resetting the active inspiration sensor 164. At this time Evtm(a), a positive-flow status is present and the Sta drive line is released, while the Sus drive line is designed to continue driving open the valve 162 using less energy than the Sta drive line. The Sus drive line continues driving the valve 162 for a predetermined amount of elapsed time Eltm(1). Once the Sus drive line has been active for its predetermined amount of time, the valve 162 is de-energized to return to a normally closed position to stop the flow of oxygen at Evtm(b). The S/D drive line will go back low if a valid inspiration effort is still occurring at Eltm(2). In other words, the oxygen flow will be terminated while the patient is still breathing in.

The microprocessor 106 will measure the time from Ie(1) to Ie(1)' to thereby determine the inspiration depth factor for each valid inspiration effort. Time mark Ie(1)' is the time at which the inspiration effort ends, and the patient is about to pause or begin breathing out. Once the valve 162 has been opened and shut, (a valve cycle), the valve will not reopen due to an inspiration event by the patient until the envelope time (Env) has elapsed. Therefore, inspiration efforts will be ignored until after Env goes low at Evtm(d). The envelope time is set according to allowable and preset inspiration rates. For example, an Envelope time of three seconds is used when a maximum allowable respiration rate is set for 20 inspiration events per minute.

After EVtm(d), the next detected and allowed inspiration effort on the S/D line occurs at Ie(3), even though an inspiration event was detected at Ie(2). Ie(2) did not trigger the Sta drive line and the Sus drive line because the inspiration event occurred during the envelope when no new inspiration events will trigger a response from the system.

Along with normal operation, the present invention is also designed to detect abnormal conditions. One of the abnormal conditions which the present invention is designed to detect is an Apnea condition, or the suspension of breathing by the patient. In the event that inspiration events should fail to be detected within a predetermined period of time, regardless of the presence of oxygen pressure, the oxygen conserving device 100 will respond with an apnea condition.

Figure 6:
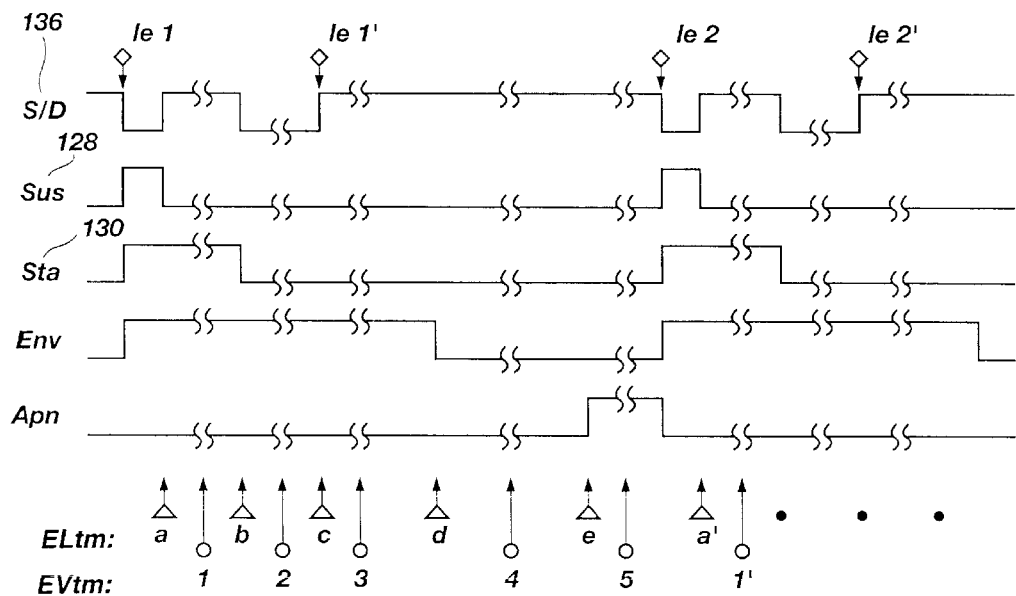
FIG. 6 is an event timing diagram showing operation of the oxygen conserving device of FIG. 1 when an apnea condition is detected.

FIG. 6 shows an event timing diagram of what occurs in the oxygen conserving device 100 when an apnea condition is determined to exist. In the presently preferred embodiment, the apnea condition is set at about 30 seconds, although this can be modified. After the envelope time has expired at ELtm(d), the timing diagram indicates that no further inspiration events are detected throughout EVtm(4). The microprocessor 106 then triggers an apnea condition alarm by sending the Apn line high at ELtm(e). The alarm may consist of an audio alarm, a visual alarm, or a combination of the two.

As mentioned previously, the oxygen conserving device 100 (FIG. 1) includes a flow fault alarm to inform the patient that the oxygen supply 110 has run out, or that the tubing between the oxygen supply 110 and the cannula has become pinched or disconnected.

Figure 7:
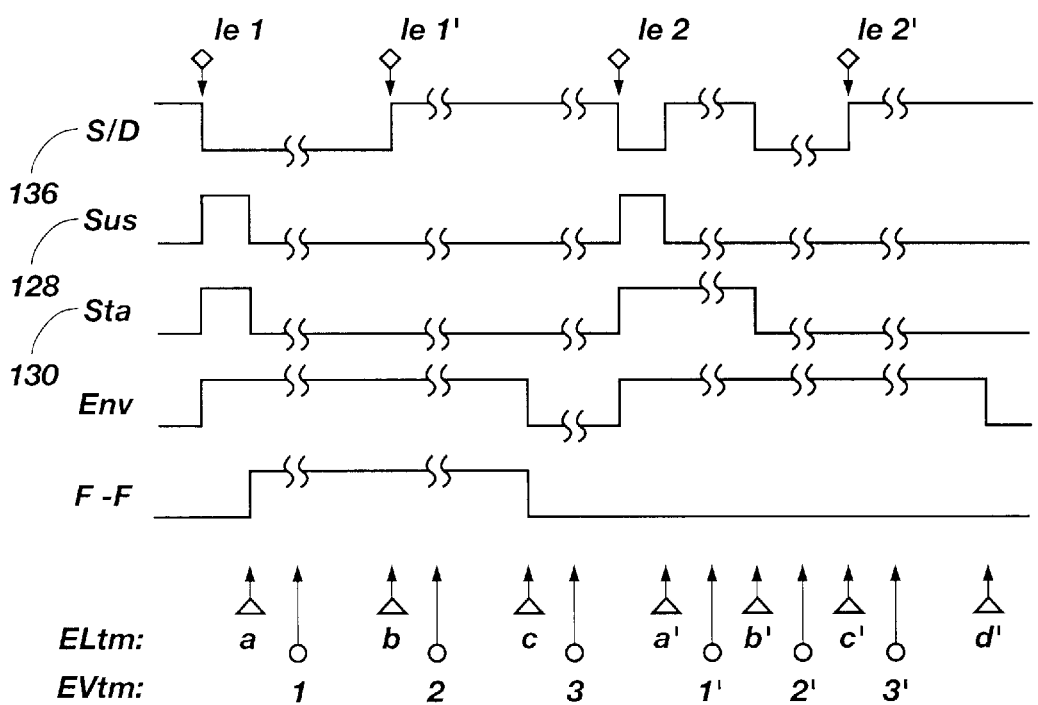
FIG. 7 is an event timing diagram showing operation of the oxygen conserving device of FIG. 1 when a flow fault condition is detected.

FIG. 7 is an event timing diagram of what occurs in the oxygen conserving device 100 when a flow fault condition is detected. In the diagram, a flow fault has been detected by the microprocessor 106 between Ie(1) and Ie(1)' as indicated by F—F going high at ELtm(a). If oxygen pressure is not present to reset the S/D sensor output line once a period of time has elapsed to where the valve opens, the S/D sensor output line remains low during the entire inspiration effort. This condition constitutes a flow fault condition when there is insufficient oxygen supply pressure. The system is designed such that the sustain drive line will go low and release the valve to move to its normally closed position on any flow fault alarm detection. Once the oxygen pressure is restored, operation of the system will return to normal as indicated beginning at Ie(2).

Figure 8:
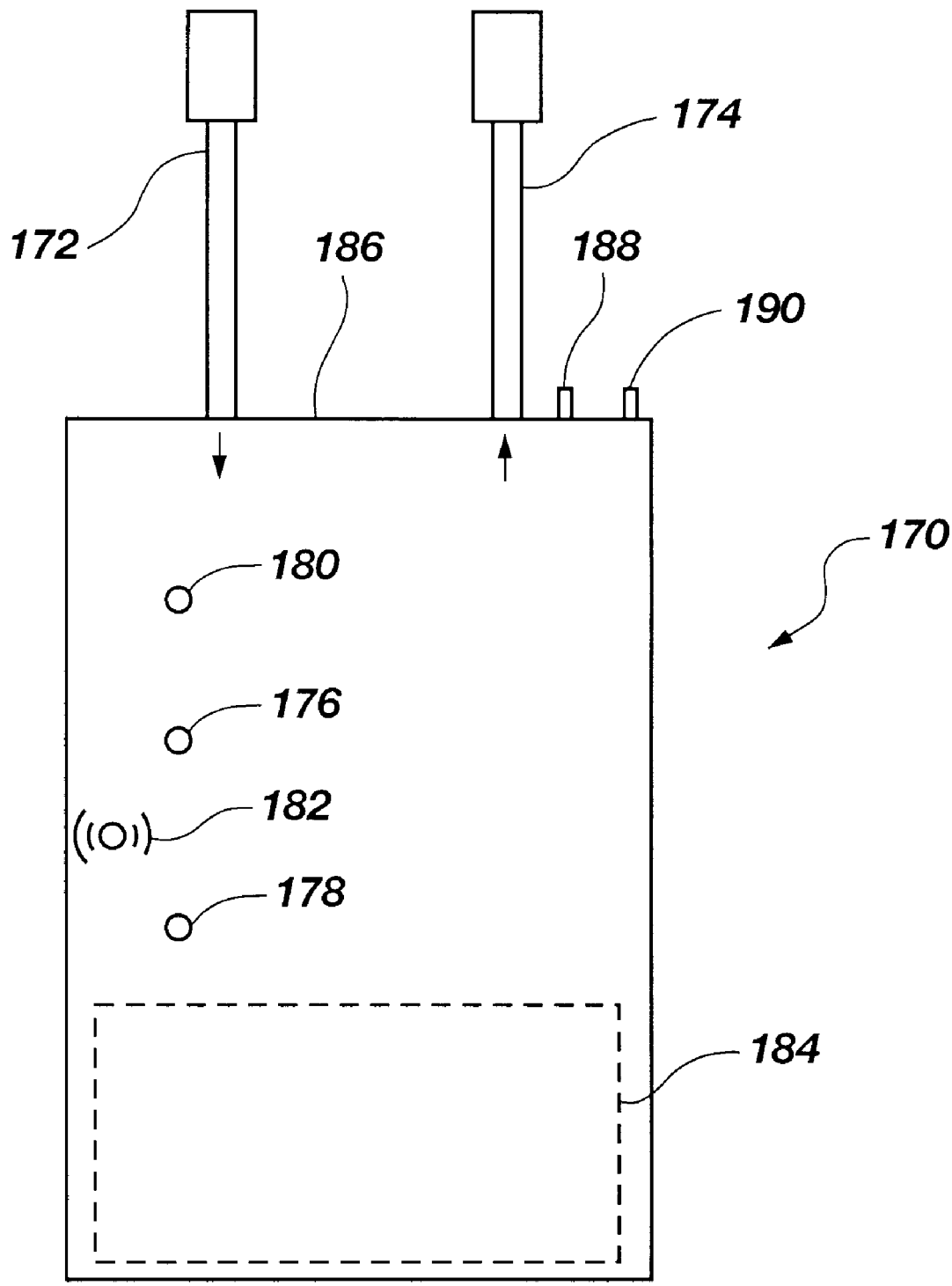
FIG. 8 is a profile view of an external packaging of the OCDS as described in the preferred embodiment of FIG. 1.

It should be apparent from the description of the oxygen conserving delivery system (OCDS) of FIG. 1 that the system can be mobile. FIG. 8 is provided as an external profile view of the OCDS in a mobile configuration. All that is externally visible on the device 170 are an inlet connection and tube 172 from the oxygen supply source, an outlet connection and tube 174 to the cannula, a flow fault and apnea condition bulb 176, a low battery bulb 178, a positive flow indicator bulb 180, and a speaker outlet 182 for an audible alarm. Shown in outline is a battery compartment 184 which is visible on a backside of the device 170. On a top side 186 of the device 170 are two buttons 188 and 190. These buttons are for increasing (button 188) and for decreasing (button 190) the effective flow rate setting of the device 170.

It is observed that what is accomplished by the presently preferred embodiment of the present invention is to provide an oxygen conserving device 100 which is capable of portable use. Alternatively, the OCDS of FIG. 1 can be modified, in an alternative embodiment, with a regulator and a bypass valve to create a single package.

Figure 9:
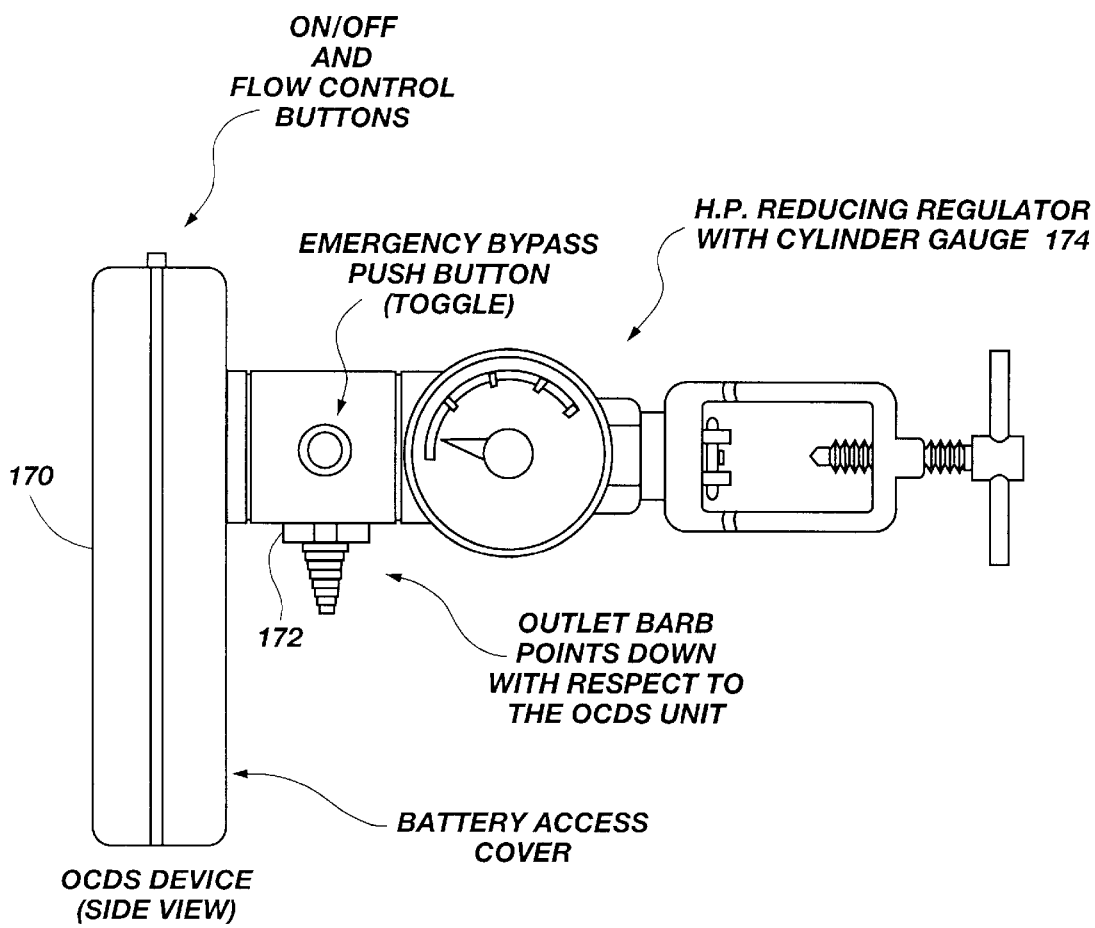
FIG. 9 is an elevational profile view of an alternative embodiment, including an oxygen conserving delivery system which is coupled to a primary H.P. reducing regulator, a bypass valve and a cylinder gauge.

This single combined system is shown in FIG. 9. The most obvious difference as compared to FIG. 8 is that the inlet connections of the OCDS of FIG. 8 are moved so that the OCDS 170 of FIG. 9 is now coupled to an H.P. reducing regulator and bypass valve 172. The OCDS 170 can be coupled to a variety of different types of regulators. This type of combined OCDS unit can be coupled to different types of oxygen cylinders. The H.P. reducing regulator low pressure outlet body parts swivel, enabling a gauge 174 on the regulator to be aligned as desired with respect to a cylinder (not shown). In addition, the OCDS 170 can be rotated and oriented as desired.

Figure 10:
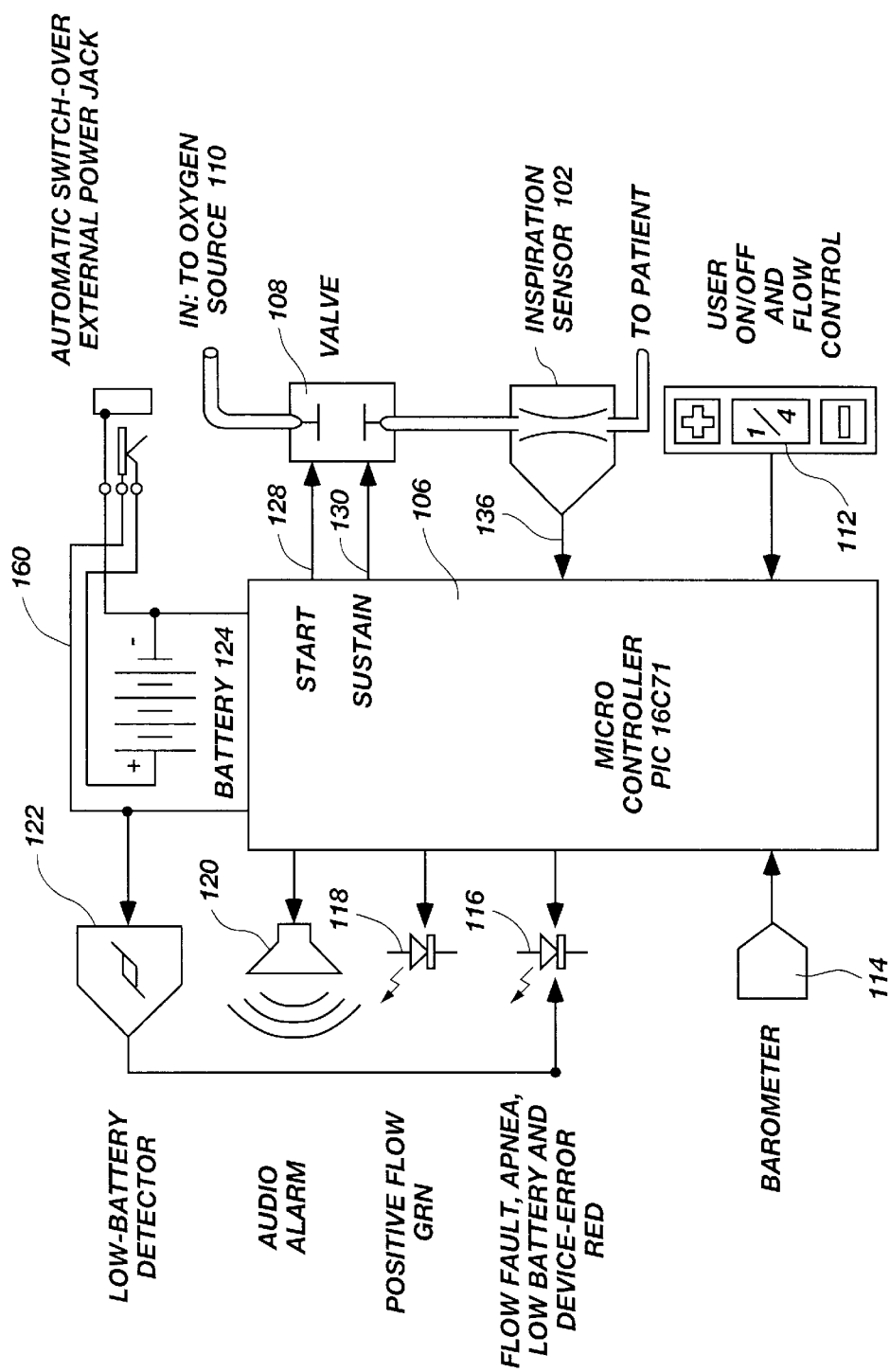
FIG. 10 is a block diagram of another alternative embodiment of the oxygen conserving delivery system which includes a barometer to enable adjustments in oxygen delivery based on changes in altitude.

FIG. 10 shows that in another alternative embodiment of the present invention, it is desirable to be able to compensate for changes in the conditions under which the OCDS 100 (FIG. 1) must operate. Accordingly, another feature that can be added is a barometer 114 which can generate an input signal to the microprocessor 106 to enable the OCDS 100 to compensate for changes in altitude (and thus availability of oxygen). The barometer 114 is used to augment the flow of oxygen to the patient and thereby compensate for moderate barometric changes such as an excursion to a mountain resort or on an airplane. The function of the barometer should not be confused with the ability of the device to adapt to changes in respiration depth and rate.

The barometer 114 is used to augment the flow of oxygen to the patient in accordance with a selectable formula. In the presently preferred embodiment, the barometer 114 provides a signal to the microprocessor indicative of changes in altitude. The flow rate of oxygen is modified by a minimum increase of 1.0 liters per minute for every increase of 10,000 ft. in altitude. This change in flow rate can be augmented by as much as 2.0 liters per minute for each increase of 10,000 ft. in altitude.

It was previously explained that the present invention responds to the entire phase of the patient's inspiration efforts and the admission cycle of the oxygen by calculating a real-time respiration depth-time factor. The OCDS contains a table in firmware that describes a delivery schedule that is indexed in two dimensions. The data in the tale is derived from known requirements of human respiratory physiology. The first index (Y) is derived from the average inspiration rate. The second index (X) is derived from the average inspiration dwell time. Using the measured inspiration rate and dwell time of the system, the OCDS compensates for changes in oxygen delivery needs based on real-time measurements.

In an alternative embodiment for providing a real-time respiration depth-time factor, the barometer is used to measure the actual inspiration depth/force, in addition to altitude. This alternative embodiment requires a data table having a third index, for the negative pressure depth of the inspiration efforts.

Figure 11:
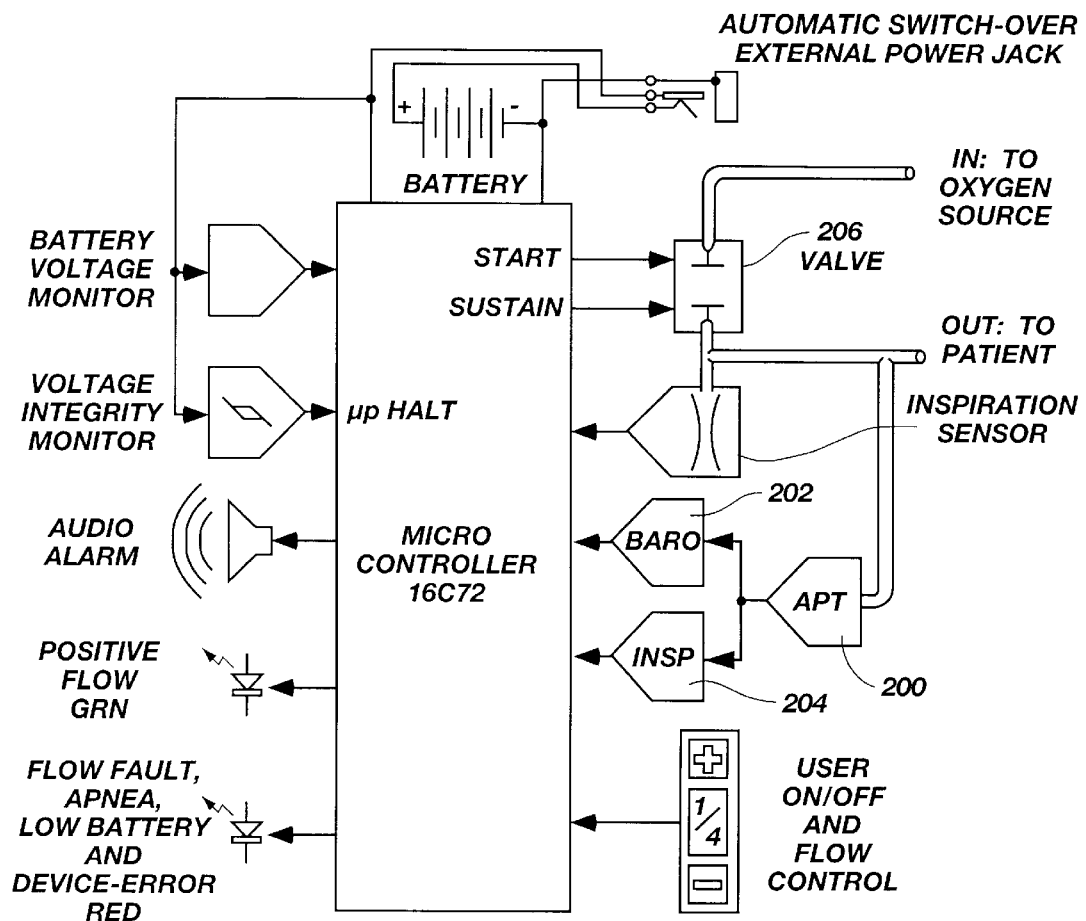
FIG. 11 is a block diagram of another alternative embodiment of the oxygen conserving delivery system which includes sensors for measuring inspiration effort depths and positive pressures caused by the opening of the valve.

FIG. 11 is a block diagram of this alternative embodiment. This embodiment utilizes an Absolute Pressure Transducer (APT) barometer device 200 where the output is coupled to two signal processing modules (or processor amplifiers). A first barometer module 202 scales a signal from the APT for altitude measuring. A second inspiration module 204 performs a track, hold and zoom function in order to measure small negative pressures produced from inspiration efforts. The physical input of the APT is also coupled to the oxygen tube that goes to the patient.

The APT enables the present invention to measure inspiration effort depths (the minute negative pressures) and positive pressures caused by the opening of the valve 206.

The microprocessor selects between the processing modules 202 and 204 at times when making the measurements does not interfere with each other. For example, the first barometer module 202 takes measurements synchronously between inspiration efforts where the outlet of the OCDS is in a static or ambient state. This means that the valve 206 is closed and the person using the device is in between an inspiration and an expiration effort, or in between inspiration efforts.

Figure 12:
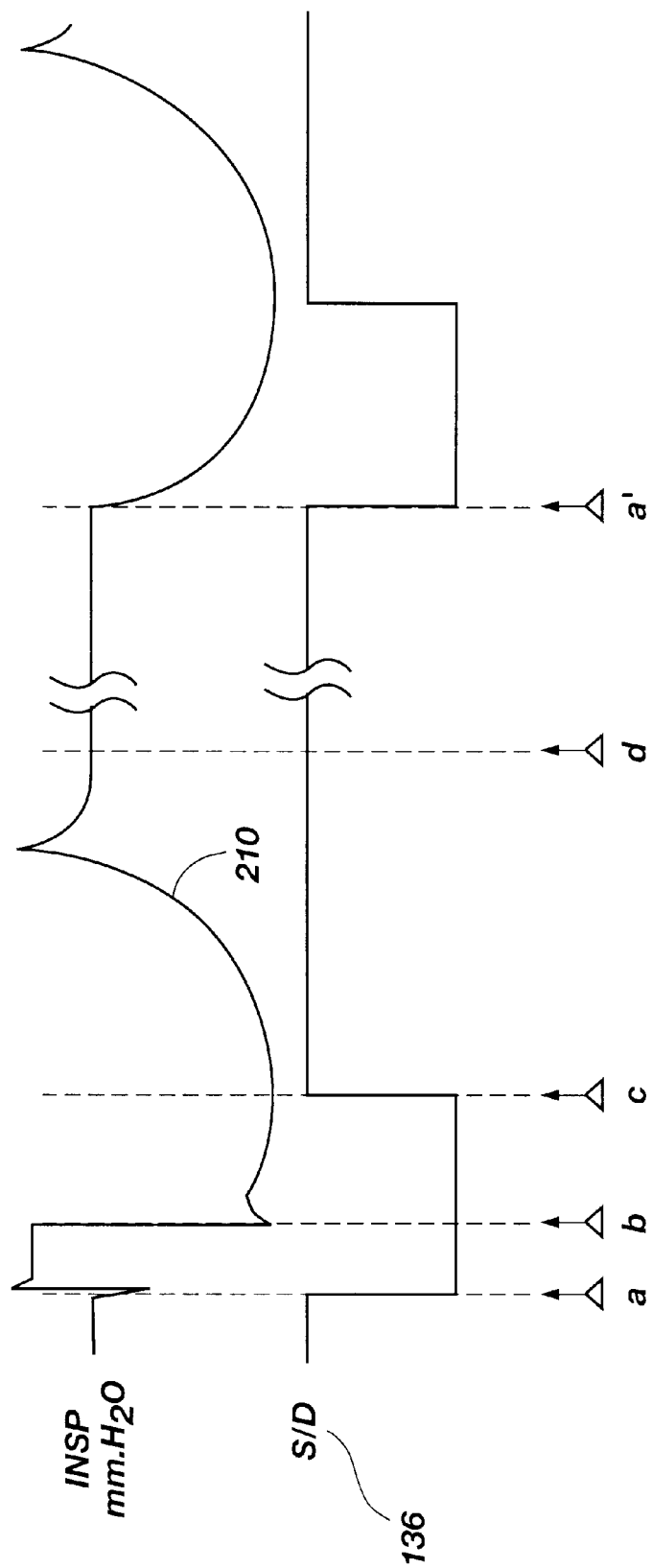
FIG. 12 is an event timing diagram of the waveform from inspiration efforts, and a sensor output line (S/D).

FIG. 12 is provided as an event timing diagram which illustrates operation of the APT 200. At event time (a), an inspiration event is beginning. Shortly thereafter (about 5 ms), the valve 206 opens at event time (b) at which time the ATP responds to the increase in pressure from the supply of oxygen from the valve 206. During the time between events (b) and (c), the microprocessor will use the last measured absolute ambient pressure reading from the first barometer module 202 as a reference, and switch to read a signal from the second inspiration module 204 where it will hold this reference and magnify and measure small variations in absolute pressures that result from inspiration efforts. The magnification of the signals is accomplished by increasing gain by a factor, in this embodiment, of 250. A profile and peak negative signal will be an analog to actual inspiration depth efforts. FIG. 12 shows the waveform 210 from inspiration efforts magnified about 250 times to show a "track and zoom" mode of operation. Event (a') illustrates an inspiration effort that occurs outside of the envelope of time during which it is measured without the interruption of the valve 206 admitting oxygen.

At event (c), the microprocessor determines (from real-time measurements of inspiration rate and dwell times) the most stable (quiet) time at which to switch to and read the signal from the first barometer module 202 to thereby make altitude measurements. The first barometer module 202 preferably has a gain factor of only 1.5. The APT 200 has a transfer function that roughly equates to a voltage range between 0.5 to 4.75 volts with an absolute pressure range of 1.15 bar to 0.015 bar (15 mb).

It is to be understood that the above-described arrangements are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. An oxygen conserving delivery system operative to regulate a flow of oxygen during an inspiration event of a respiratory cycle, and comprising:

a valve assembly including a valve for receiving oxygen, and having an output port;

an inspiration sensor assembly coupled at a first port to the output port of the valve assembly, having a second port;

a signal generator for generating a signal on a sensor output line of the inspiration sensor assembly when an inspiration event is detected by the inspiration sensor assembly;

a single respiration tube coupled to the second port of the inspiration sensor assembly;

a microcontroller for regulating operation of the oxygen conserving delivery system, wherein the microcontroller is coupled to the valve assembly via a start drive line which when actuated provides sufficient power to the valve assembly to initially open the valve, and coupled to the valve assembly via a sustain drive line which when actuated provides less power to the valve assembly suffering only to maintain the valve in an open position, and wherein the microcontroller receives input from the sensor output line when the inspiration event is detected;

a power source for providing power to the oxygen conserving delivery system; and a means for regulating a respiration rate of oxygen supplied by the oxygen conserving delivery system between no delivery of oxygen and a maximum delivery rate of oxygen.

2. The oxygen conserving delivery system as defined in claim 1 wherein the system further comprises a plurality of status indicators to provide feedback to an operator of the system of a status thereof.

3. The oxygen conserving delivery system as defined in claim 2 wherein the plurality of status indicators are comprised of:

a plurality of visual status indicators; and an audio status indicator, wherein the audio status indicator can provide a same type of information to the operator as is provided by the plurality of visual status indicators.

4. The oxygen conserving delivery system as defined in claim 3 wherein the plurality of visual status indicators further comprises:

a flow fault status indicator which is actuated when a flow of oxygen to the patient is interrupted;

an apnea status indicator which is actuated when the inspiration sensor assembly does not detect a second inspiration event within a predetermined time period after detecting a first inspiration event; and a positive flow status indicator which is actuated by normal operation of the oxygen conserving device, and which functions to at least provide feedback to the operator that said system is functioning properly.

5. The oxygen conserving delivery system as defined in claim 4 wherein the system further comprises a dedicated low battery detection circuit for determining when the battery is providing voltage below the predetermined voltage level.

6. The oxygen conserving delivery system as defined in claim 3 wherein the plurality of visual status indicators further comprises:

a low battery status indicator which is actuated when a battery providing power to the system falls below a predetermined voltage level; and a voltage integrity indicator which is actuated when the voltage to the oxygen conserving delivery system is not being consistently delivered such that normal operation cannot be guaranteed.

7. The oxygen conserving delivery system as defined in claim 3 wherein the microcontroller includes a memory for storing a plurality of different signals which when used to drive the audio status indicator, can provide audibly distinct sounds, each of which is associated with a particular condition of said system.

8. The oxygen conserving delivery system as defined in claim 1 wherein the power source further comprises a battery so that the oxygen conserving delivery system is mobile.

9. The oxygen conserving delivery system as defined in claim 8 wherein the valve assembly further comprises means for reverse shunting reflected electromotive energy from the valve back to the battery.

10. The oxygen conserving delivery system as defined in claim 9 wherein the means for reverse shunting electromotive energy further comprises using quenching arrestors to thereby eliminate any potential for a spark which must be prevented when operating in an oxygen rich environment.

11. The oxygen conserving delivery system as defined in claim 1 wherein the inspiration sensor assembly further comprises:

a first stationary plate;

a second stationary plate;

a canter plate which capacitively couples the first stationary plate to the second stationary plate, wherein a increase in pressure results in an increase in capacitively coupled current to flow from the first stationary plate to the second stationary plate, wherein a decrease in pressure results in a decrease in capacitively coupled current to flow from the first stationary plate to the second stationary plate, and wherein the canter plate is electrically coupled to a full-wave rectifier and current amplifier.

12. The oxygen conserving delivery system as defined in claim 11 wherein the inspiration sensor assembly further comprises:

a first comparator for generating a repetitive signal to thereby excite the first stationary plate; and a second comparator for generating an output signal which transitions from a first state to a second state when an inspiration event is detected, and which transitions from the first state to the second state when 1) gas pressure from the valve, when said valve is open, resets the canter plate, or 2) the inspiration sensor assembly detects an end of an inspiration effort.

13. The oxygen conserving delivery system as defined in claim 1 wherein the inspiration sensor assembly further comprises:

an excitation circuit for providing a predetermined clock signal;

an inspiration sensor for receiving input from the excitation circuit, and which is sensitive to pressure changes which cause the inspiration sensor to generate a first output signal which is indicative of pressure thereon;

a first rectifying and buffering circuit for processing a positive half of the first output signal and thereby generating a second output signal;

a first low pass filter which receives the second output signal and generates a third output signal;

a first high pass filter which receives the third output signal and generates a fourth output signal;

a positive reference signal which is modified by the fourth output signal to thereby generate a fifth output signal; and a detector circuit for receiving the fifth output signal and capable of detecting pressure changes in the inspiration sensor that are indicative of an inspiration effort.

14. The oxygen conserving delivery system as defined in claim 13 wherein the inspiration sensor assembly further comprises:

the inspiration sensor for receiving input from the excitation circuit, and which is sensitive to pressure changes which cause the inspiration sensor to generate a first output signal which is indicative of pressure thereon;

a second rectifying and buffering circuit for processing a negative half of the first output signal and thereby generating a sixth output signal;

a second low pass filter which receives the sixth output signal and generates a seventh output signal;

a second high pass filter which receives the seventh output signal and generates an eighth output signal;

a negative reference signal which is modified by the eighth output signal to thereby generate a ninth output signal; and the detector circuit for receiving the ninth output signal and capable of detecting pressure changes in the inspiration sensor that are indicative of an inspiration effort.

15. The oxygen conserving delivery system as defined in claim 1 wherein the system further comprises a barometer for detecting changes in altitude, wherein the barometer provides a signal to the microcontroller when a sufficient change is detected in altitude to warrant a modification in oxygen delivery to the patient.

16. The oxygen conserving delivery system as defined in claim 1 wherein the valve is further comprised of a valve which is normally closed.

17. The oxygen conserving delivery system as defined in claim 1 wherein the system further comprises:

a memory for the microcontroller which once programmed cannot be erased, and which stores program instructions for controlling the microcontroller; and a look-up data table stored in the memory and which contains data regarding an oxygen delivery schedule that is responsive to an index of average inspiration rates and average inspiration dwell times.

18. The oxygen conserving delivery system as defined in claim 17 wherein the system further comprises the look-up data table stored in the memory which also contains data regarding an index of inspiration depths to thereby obtain the oxygen delivery schedule.

19. A method for supplying oxygen to a patient's respiratory system during a respiration cycle which includes inhalation, said method comprising the steps of:
  (1) providing an oxygen conserving delivery system which includes a valve assembly, an inspiration sensor assembly, a microcontroller for positively controlling operation of the valve assembly and the inspiration sensor assembly, and a power source for mobile operation of said system;
  (2) providing sufficient energy to open a valve of the valve assembly; and
  (3) providing a lesser amount of energy to the valve assembly when the valve is completely opened, wherein said lesser amount of energy is sufficient to maintain the valve in an open position until the microcontroller determines that the valve is to be closed, and wherein said method of opening the valve compensates for variations in power source condition, inlet pressures to the system, variations in valve tolerances, and an absence of oxygen pressure.

20. The method as defined in claim 19 wherein the method further comprises the steps of:
  (1) reverse shunting reflected electro-motive energy from the valve back to the battery; and
  (2) eliminating a possibility of a spark resulting from power being released from transistors that are supplying energy to open the valve, by providing quenching resistors in a circuit providing the reverse shunting.

* * * * *